United States Patent [19]

Quaranta et al.

[11] Patent Number: 5,422,264
[45] Date of Patent: Jun. 6, 1995

[54] SOLUBLE FACTOR STIMULATION OF ATTACHMENT AND HEMIDESMOSOME ASSEMBLY IN EPITHELIAL CELLS

[75] Inventors: Vito Quaranta, La Jolla; Marketta Hormia, San Diego, both of Calif.

[73] Assignee: Desmos, Inc., San Diego, Calif.

[21] Appl. No.: 151,134

[22] Filed: Nov. 12, 1993

[51] Int. Cl.$^6$ .............................................. C12N 5/00
[52] U.S. Cl. ................................ 535/240.2; 435/240.1
[58] Field of Search ............................ 435/240.1, 240.2

[56] References Cited

U.S. PATENT DOCUMENTS 5,273,900 12/1993 Boyce ............................ 435/240.23

FOREIGN PATENT DOCUMENTS 9217498 10/1992 WIPO .
9405316 3/1994 WIPO .

OTHER PUBLICATIONS

Hormia, et al. "The Distribution of Integrin $\alpha_6\beta_4$ in Keratinocytes is Modulated by Rat Carcinoma Cells", *International Association for Dental Research*, Feb. 1993, Abstract, 1 page.

Jones, et al. "$\alpha_6\beta_4$ Integrins: Their Role in the Assembly of the Hemidesmosome (HD) and in Signal Transduction", *J. Cell. Biochem.*, Supplement 16F: Apr., 1992.

Langhofer, et al. "Matrix Signals Transduced by the $\alpha_6\beta_4$ Integrin Complex", *Mol. Biol. Cell.*, 3, Supplement: 95a, Sep., 1992.

Riddelle, et al. "Substrate Attachment is Necessary for the Expression of Hemidesmosomal Proteins in Cultured Cells", *Mol. Biol. Cell.*, 3, Supplement: 70a, 1992.

Riddelle, et al., "Characterization of a Novel Cell–Substratum Attachment Device in Cultured Epithelial Cells", *J. Cell. Biol.*, 109: 201a, 1989.

Riddelle, et al. "Dynamic Aspects of Hemidesmosomes in the Novel Epithelial Cell Line, 804G", *J. Cell. Biol.*, 115: 41a, 1991.

Hopkinson, et al. "Expression of Hemidesmosomal Plaque Components", *J. Cell. Biol.*, 111: 408a, 1990.

Riddelle, et al. "Hemidesmosomes in Cultered Cells", *J. Cell. Biol.*, 111: 408a, 1990.

Kurpakus, et al. "Integrins in the Hemidesmosome", *J. Cell. Biol.*, 111: 402a, 1990.

Schwartz, et al. "Desmosomes and Hemidesmosomes: Constitutive Molecular Components", *Annu. Rev. Cell. Biol.*, 6: 461–91, 1990.

Jones, et al. "Intermediate Filament–Plasma Membrane Interactions", *Curr. Opin. Cell Biology*, 3: 127–132, 1991.

Chapman, et al., "Abnormal Expression of Hemidesmosome–Like Structures by Junctional Epidermolysis Bullosa Keratinocytes in Vitro", *British Journal of Dermatology*, 123: 137–144, 1990.

Giudice, et al., "Identification of Collagen Domains within the Bullous Pemphigoid Autoantigen, BP180", *J. Clin. Invest.*, 87: 734–738, 1991.

Hieda, et al., "Idenficiation of a New Hemidesmosomal Protein, HD1: A Major, High Molecular Mass Component of Isolated Hemidesmosomes", *The Journal of Cell Biology*, 116: 1497–1506, 1992.

Izumi, et al. "In Vitro Induction of Ornithine Decarboxylase in Urinary Bladder Carcinoma Cells", *Cancer Research*, 41: 405–409, 1981.

Kurpakus, et al. "Surface Relocation of $\alpha_6\beta_4$ Integrins and Assembly of Hemidesmosomes in an In Vitro Model of Wound Healing", *The Journal of Cell Biology*, 115:1737–1750, 1991.

Staehelin, "Structure and Function of Intercellular (List continued on next page.)

Primary Examiner—Marian C. Knode
Assistant Examiner—Kristin Larson
Attorney, Agent, or Firm—Knobbe, Martens, Olson, & Bear

[57] ABSTRACT

A method for growing epithelial cells in vitro using soluble proteins secreted by 804G rat bladder carcinoma cells. These proteins are able to stimulate cell attachment and hemidesmosome formation in cells grown in contact with the proteins. The purification of these proteins from 804G culture supernatant is greatly facilitated by culturing the cells under low serum conditions.

3 Claims, No Drawings

OTHER PUBLICATIONS

Junctions", Department of Molecular, Cellular and Developmental Biology, University of Colorado, Boulder, Colo.: 191–283.

Stepp, et al., "$\alpha_6\beta_4$ Integrin Heterodimer is a Component of Hemidesmosomes", *Proc. Natl. Acad. Sci. USA*, 87: 8970–8974, 1990.

Sonnenberg, et al., "Integrin $\alpha_6/\beta_4$ Complex is Located in Hemidesmosomes, Suggesting a Major Role in Epidermal Cell–Basement Membrane Adhesion", *The Journal of Cell Biology*, 113: 907–917, 1991.

Hopkinson, et al., "Cytoplasmic Domain of the 180–kD Bullous Pemphigoid Antigen, A Hemidesmosomal Component: Molecular and Cell Biologic Characterization", *J. Invest. Dermatol.:* 264–270, 1992.

Langhofer, et al., "The Matrix Secreted by 804G Cells Contains Laminin–Related Components that Participate in Hemidesmosome assembly in Vitro", *Journal of Cell Science*, 105: 753–764, 1993.

SOLUBLE FACTOR STIMULATION OF ATTACHMENT AND HEMIDESMOSOME ASSEMBLY IN EPITHELIAL CELLS

GOVERNMENT SUPPORT

This research was supported by National Institutes of Health Grants GM 46902 and DE 10063. The government may have certain rights in the invention.

BACKGROUND

When organs of the body are formed, they develop in neatly organized arrays. Often, cell groups of one kind are separated from cells of another kind by flat strips of connective tissue called basement membranes. In skin, for instance, the superficial layer of epidermal cells adheres to the underlying basement membrane. This skin basement membrane acts as a barrier between the epidermal cells on the outside, and the dermal cells underneath. A similar arrangement of cells occurs in the lining of the gut.

Basement membranes have been implicated in the growth, attachment, migration, repair, and differentiation of their overlying cell populations. Three layers have been defined in basement membranes: a) the lamina lucida, an electron microscope-clear region that resides in close approximation to the overlying cells; b) the lamina densa, an electron dense region of 20-300 nm in width; and c) the sublamina densa that contains anchoring fibrils, microfibrillar bundles and collagen fibers.

Many different types of compounds have now been localized to the basement membrane. Some of these compounds are laminin, collagen IV and heparin sulfate proteoglycans (Verrando et al. *Exp. Cell Res.* (1987); 170: 116-128). In addition, specific basement membranes have been found to possess other compounds, such as nidogen and entactin.

The principal cell adhesion receptor that epidermal cells use to attach to the basement membrane is called $\alpha_6\beta_4$. This transmembrane receptor is formed by a combination of two protein moieties $\alpha_6$ and $\beta_4$. The $\alpha_6$ and $\beta_4$ proteins are derived from different genes that have been found to be part of the integrin family.

Integrins are versatile family cell adhesion receptors. So far, approximately twenty members have been discovered in the integrin family. These molecules are involved in many types of cell adhesion phenomena in the body. Integrins are signalling molecules that can translate environmental cues into cellular instructions. Further, integrins can also transmit signals in the reverse direction, from the cell interior to the exterior. This has been illustrated in non-adherent cells, such as lymphocytes.

Stimulation of the T-cell antigen receptor, or of the CD3 complex, augments the affinity of certain integrins for their respective ligands. Unfortunately, in adherent cells, changes in the affinities of integrins have been more difficult to demonstrate. However, affinity modulation of one integrin in differentiating epidermal keratinocytes has been described by Adams et al. (*Cell* (1990); 63: 425-435). For this reason, modifications of cell status initiated by activation or differentiation of other receptors may influence integrin affinity, and ultimately, the adhesive behavior of cells. Further, as a consequence of adhering to a surface, an integrin may actively contribute to modifying cell shape or migration.

Many epithelial cells interact with the underlying extracellular matrix via a junction called the hemidesmosome (Staehelin, (1974) *Structure and Function of Intercellular Junctions*, Department of Molecular, Cellular and Developmental Biology, University of Colorado, Boulder, Colo., 191-283). Over the last few years there has been considerable progress in the biochemical characterization of this junction (Schwarz et al., (1990) *Annu. Rev. Cell Biol.*, 6:461-491). The hemidesmosome, with its associated structures such as intermediate filaments and anchoring fibrils, forms an adhesion complex. Disruptions of the epithelial-connective tissue interaction is often accompanied by a disruption of the hemidesmosome complex. For example, in certain blistering skin diseases such as junctional epidermolysis bullosa where epithelial cell-connective tissue interactions is abnormal, it has been proposed that there is a biochemical modification in or loss of a basement membrane zone-associated component of the hemidesmosome.

Two high molecular weight intracellular components of the hemidesmosome have been identified and characterized with the aid of antisera from patients suffering from bullous pemphigoid. This autoimmune disease results in a disruption of the interactions between epithelial cells and connective tissue simultaneously with loss of hemidesmosome integrity (Chapman et al. *Br. J. Dermatol* (1990); 123: 137-144). Accordingly, it was discovered that bullous pemphigoid patients were producing antibodies against hemidesmosome components. Two hemidesmosome related bullous pemphigoid (BP) antigens have been previously described (Klatte et al., (1989) *J. Cell Biol.*, 109:3377-3390).

One BP antigen is a 230 kD polypeptide that may act as an anchor for cytoskeleton elements in the hemidesmosomal plaque (Jones and Green, (1991) *Curr. Opin. Cell Biol.*, 3:127-132). A second BP antigen is a type II membrane protein that possesses a collagen-like extracellular domain (Giudice et al., (1991) *J. Clin. Invest.*, 87:734-738). (Hopkinson et al., (1992) *J. Invest. Dermatol.*, 3:264-270). In addition, it has been demonstrated that the interaction of the hemidesmosome with the underlying connective tissue involves the $\alpha_6\beta_4$ integrin heterodimer (Steppet al., (1990), *Proc. Natl. Acad. Sci. USA*, 87:8970-8974; Jones et al., (1991) *Cell Regulation*, 2:427-438; Sonnenberg et al., (1991) *J. Cell Biol.*, 113:907-917; Kurpakus et al., (1991) *J. Cell Biol.*, 115:1737-1750). The $\alpha_6\beta_4$ heterodimer has been localized to hemidesmosomes along the basal surfaces of the rat bladder carcinoma cell line 804 G (Jones et al. *Cell Regulation* (1991); 2: 427-438). These results suggested that integrins (e.g. $\alpha_6\beta_4$) may play an important role in the assembly and adhesive functions of hemidesmosomes.

Various prior art efforts have focused on purifying adhesion-facilitating proteins found in basement membranes. For example, Burgeson, et al., Patent Cooperation Treaty Application No. WO92/17498, disclose a protein which they call kalinin. Kalinin is said to facilitate cell adhesion to substrates; however, this material is apparently inactive with respect to hemidesmosome formation. See also, Marinkovich, et al., *J. Cell Biol.* (1992); 119:695-703 (k-laminin); Rouselie, et al., *J. Cell Biol.* (1991); 114:567-576 (kalinin); and Marinkovich, et al., *J. Biol. Chem.* (1992); 267:17900-17906 (kalinin).

Similarly, a basement glycoprotein of about 600 kD made up of polypeptides in the range of 93.5 kD to 150 kD has been identified, and is known as GB3 or nicein. See, e.g., Verrando, et al., *Biochim. Biophys. Acta* (1988); 942:45–56; and Hsi, et al., *Placenta* (1987); 8:209–217. None of these materials have been effective in generating formation of hemidesmosomes, either in vitro or in vivo.

When cultured on tissue culture plastic in vitro, most epithelial cells do not assemble bona fide hemidesmosomes despite the fact that they appear to express all of the hemidesmosomal plaque and transmembrane components mentioned above. Indeed, it is only recently that cell lines such as 804G were discovered to have the ability to readily assemble hemidesmosomes in vitro under regular culture conditions (Riddelle et al., (1991) *J. Cell Biol.*, 112:159–168; Hieda et al., (1992) *J. Cell Biol.*, 116:1497–1506). Such cells are at last allowing detailed cell and biochemical analysis of the dynamics of hemidesmosome assembly.

For instance, it has been reported that substratum-associated staining by anti-hemidesmosome antibodies is greatly diminished in 804G cell cultures that enter in vitro wound sites (Riddelle et al., *J. Cell Sci.* (1992); 103: 475–490). However, as closure of the wound became complete, anti-hemidesmosome staining along the substratum-attached surface was evident in the cells.

There are, however, many epithelial cells that do not attach to tissue culture dishes in a normal fashion, even after treatment with various growth factors. These cells do not produce normal hemidesmosomes or grow to resemble their in vivo phenotype. It would provide a tremendous advantage to have a system that was capable of maintaining epithelial cell growth in vitro wherein the cells maintained their normal phenotype.

SUMMARY OF THE INVENTION

One aspect of the present invention provides a method for inducing hemidesmosome formation in epithelial cells in vitro by the following steps:
  growing a first sample of epithelial cells in media under conditions that promote secretion of hemidesmosome-formation facilitating soluble factors, whereby the first cells secrete the factors into the media;
  removing the media from the epithelial cells; and
  growing a second sample of epithelial cells of a different type in contact with the media whereby the second epithelial cells are induced to attach to a substrate and produce hemidesmosomes.

Preferably, the second epithelial cells are human and the medium is Modified Eagles Medium. The invention also includes culturing the 804G cells in Dulbecco's Modified Eagles Medium OPTI-MEM medium in a 1:1 ratio in the presence of 1% fetal calf serum. Another embodiment provides the 804GMHcell line produced upon culturing in low serum medium. Preferably, the first epithelial cells are either 804G or NBT-II rat bladder carcinoma cells.

Another embodiment of the present invention is a method for growing epithelial cells in vitro by the following steps:
  growing 804G rat bladder carcinoma cells in media under conditions that promote the secretion of soluble factors, whereby the 804G cells secrete the factors;
  removing the media from the 804G cells; and contacting the media with epithelial cells, whereby the contact promotes hemidesmosome formation in the epithelial cells.

Preferably, the epithelial cells are mammalian; most preferably, they are human skin cells.

The present invention also includes a biocompatible shaped article adapted for use in vivo in a mammal, and a hemidesmosome formation-facilitating protein composition on the shaped article. Preferably, the protein composition is secreted by a tumor cell line of epithelial origin and the tumor cell line is either the rat bladder carcinoma cell line 804G or NBT-II.

Still another embodiment of the present invention is a composition for use in growing mammalian cells consisting of media preconditioned by growth of 804G or 804GMH cells, the media having the property of promoting hemidesmosome formation in cells contacting the media.

DETAILED DESCRIPTION

The present invention includes the discovery that a soluble factor secreted into the growth media by certain cell lines can stimulate cellular adhesion and hemidesmosome assembly in epithelial cells. One type of cell with this ability is the rat bladder carcinoma cell line 804G. This cell line has been described by Izumi, et al., *Cancer Res.* (1981); 41:405–409, and is maintained in permanent collection in the laboratory of inventor Jonathan C. R. Jones, from whom the cell line is readily available. This cell line is also available from Ryoichi Oyasu, Department of Pathology, Northwestern University Medical School, Chicago, Ill. The 804G cell line is also maintained as a Budapest Treaty patent deposit by the American Type Culture Collection (ATCC), Rockville, Md., under accession number ATCC CRL 11555 made Feb. 24, 1994. Furthermore, the purification of these soluble factors is greatly facilitated by culturing the 804G cells under low serum conditions due to the virtual absence of contaminating serum proteins. Although the 804G cells were cultured in Dulbecco's Modified Eagles Medium:OPTI-MEM (1:1) in the presence of 1% fetal calf serum, the use of other media and other concentrations of fetal calf serum, preferably from about 0.1% to about 5%, is also contemplated.

Ultrastructural data have been developed demonstrating that the 804G soluble factor can induce a number of different cell types to develop mature hemidesmosomes and attach to their growth substrate. A solution can now be prepared, having factors secreted by cells such as 804G cells, that can modulate the organization of hemidesmosomal antigens in unrelated cells. This effect appears specific to hemidesmosomal elements since adhesion plaque components do not obviously change their localization in cells treated with the 804G soluble factor.

To demonstrate our new discovery, we provide evidence that the murine 804G factor was capable of inducing assembly of "mature" hemidesmosomes in human HaCaT cells. It can be appreciated that it is uncommon to find compounds from murine cells that have such a profound effect on human tissue. In the experiments described in more detail below an increased number of hemidesmosome-like structures were found in HaCaT cells treated with 804G growth media, as compared to control experiments wherein HaCaT cells were grown on rat tail collagen. Moreover, the majority of hemidesmosome-like structures in the treated cells contacted the cell-substrate and possessed basal dense plates. The basal dense plate structures are often used as indicators of mature or formed hemidesmosomes (Krawczyk and Wilgram, (1973) *J. Ultrastruct. Res.*, 45:93-101).

Although methods relating to production and isolation of the 804G soluble factor are disclosed, it can be appreciated that any cell that secretes compounds transmitting the ability to support cell adhesion and hemidesmosome assembly in vitro is within the scope of the present invention. Soluble factors from other cell types, such as the murine bladder carcinoma cell line NBT-II (ATCC CRL 1655), also appear able to induce attachment and hemidesmosome assembly in vitro. The NBT-II cell line is also maintained as a Budapest Treaty patent deposit by the American Type Culture Collection (ATCC), Rockville, Md., under accession number ATCC CRL 11556 made Feb. 24, 1994. It should be noted that the term "804G Factor" is used herein to generically refer to any secreted cell factor with the ability to stimulate cell attachment and hemidesmosome formation.

One major use contemplated for the active components of the soluble material is in cell growth and attachment. A substrate upon which cells are to be grown is coated with a solution comprising the soluble factor. The cells to be grown are then plated or applied to the substrate. Such cells, including human cells in vitro and in Wvo, will grow in an organized fashion on the substrate and will form hemidesmosomes. Hemidesmosome formation is a major advantage, because it greatly enhances the attachment of the cells to the substrate. Furthermore, it appears that the organization of cells stimulated by the soluble factor is significantly more advanced, more tissue-like, than cells grown without stimulation by the active components in the secreted factors of the present invention.

The substrate used herein may be any desired substrate. For laboratory use, the substrate may be as simple as glass or plastic. For use in vivo, the substrate may be any biologically compatible material on which cells can grow. Suitable substrate materials may include shaped articles made of or coated with such materials as collagen; regenerated collagen; polylactic acid; biocompatible metals such as stainless steel and titanium; ceramic materials including prosthetic materials such as hydroxylapatite; synthetic polymers, including polyesters and nylons; and virtually any other material to which biological molecules can readily adhere.

One particular use of the present invention is to increase epidermal cell adhesion to target surfaces. For instance, prostheses for dental implantation may be coated with the 804G soluble factor to stimulate periodontal cell attachment. Existing teeth may similarly be coated as a treatment for gum (junctional epithelium) disease, such as gingivitis. Where a substrate is made of polymers of natural or synthetic bioerodible material in the form of a sheet or fabric, such as woven or bonded collagen, polylactic acid, lactide, glycolide, glutamic acid, collagen or albumin the matrix materials may be applied to the surface thereof or mixed in with the composition. Cells (such as epidermal cells) may then be grown on the matrix ex vivo to form transplantable or implantable materials; alternatively, the materials may be implanted and cells may be permitted to attach in vivo.

The 804G soluble factor will also be of great use in studies concerning hemidesmosome morphogenesis and $\alpha_6\beta_4$ integrin interactions with the epithelial extracellular matrix. Indeed, the active factors secreted by the 804G cells may prove to be a tool that allows definition of hemidesmosome-mediated interactions between epithelial cells and their underlying connective tissues at the molecular level.

In addition to the soluble factor and the active components thereof, the present invention also includes shaped articles coated with those materials. Preferably, those shaped articles are formed of materials other than glass, and include such forms as sheets, fabrics, prostheses, metal articles, bioerodible articles, and implantable articles.

Furthermore, pharmaceutical preparations having the soluble factor are contemplated. These preparations can be in any suitable form, and generally comprise the active ingredient in combination with any of the well known pharmaceutically acceptable carriers. The soluble factor may be isolated from the growth media in which appropriate cells have been grown. Alternatively, the soluble factor may be prepared synthetically or through recombinant DNA techniques, or through purification of isolated proteins from the growth media.

Carriers can include injectable carriers, topical carriers, transdermal carriers, and the like. The preparation may advantageously be in a form for topical administration, such as an ointment, gel, cream, spray, dispersion, suspension, or paste. The preparations may further advantageously include preservatives, antibacterials, antifungals, antioxidants, osmotic agents, and similar materials in composition and quantity as is conventional. For assistance in formulating the compositions of the present invention, one may refer to Remington's Pharmaceutical Sciences, 15th Ed., Mack Publishing Co., Easton Pa. (1975), the relevant disclosure of which is hereby incorporated by reference.

Finally, epithelial cells of various types may be grown in contact by the compositions contemplated herein.

As a first step in discovering the properties of the 804G soluble factor, HaCaT cells were treated with media from growing 804G cells.

EXAMPLE 1

Soluble Factor Treatment of HaCaT Cells

The immortalized human keratinocyte cell line HaCaT, provided by Dr. Norbert Fusenig, Heidelberg, Germany (Boukamp et al., (1988) *J. Cell Biol.*, 106:761-771), was cultured in DMEM medium (Bio-Whittaker, Walkersville, Md.) supplemented with 10% fetal calf serum (FCS, Bio-Whittaker) and antibiotics. The HaCaT cell line has normal keratinization properties in vitro, is positive for involucrin, filaggrin, cytokeratins 1, 10, 5, 6, 14, 16/17, 7, 8 and 19 and is negative for vimentin. Thus it has characteristics very similar to primary keratinocytes.

The rat bladder carcinoma cell line, 804G, and the human embryonic fibroblast cell line WI-38 (ATCC #CCL 75) were also cultured in DMEM medium with the same supplements.

Culture supernatant of 804G cells was collected from cultures that were approximately 70% confluent and reached confluence over a 48 hour period. At the end of this time 15 mls of supernatant was collected from a 75 cm$^2$ culture flask. Supernatant of HaCaT and WI-38 cells were collected in the same manner over a 48 hour period.

HaCaT cells plated on tissue culture plastic in normal medium attach, spread very slowly, and still appear rounded 2 hours after seeding. In contrast, however, when the cells were seeded in the culture supernatant of 804G cells they attached to the growth substratum and acquired a flattened morphology within 30 minutes. After 24 hours, cells in normal medium formed epithelioid islands whereas cells seeded in supernatant from 804G cells exhibited a spread-out morphology and appeared to migrate so as to uniformly cover the growth substratum. The 804G culture supernatant effect was evident even if the cells were plated in a 1:1 dilution of the supernatant with normal medium. As a control, HaCaT cells were also plated in their own culture supernatant and in medium collected from cultures of human fibroblasts (WI-38). HaCaT cells plated in either their own medium or WI-38 medium did not exhibit the growth and morphology of those cells plated in 804G medium.

We then performed the following experiments to analyze the affect of the 804G supernatant on hemidesmosome elements in the HaCaT cells.

EXAMPLE 2

Analysis of Hemidesmosome Development After Treatment with the 804G Supernatant

To study the effect of 804G culture supernatants on the distribution of $\alpha_6\beta_4$ integrins, HaCaT cells were grown on glass coverslips, fixed and immunolabeled for $\alpha_6$ and $\beta_4$ integrin subunits, hemidesmosomal components, or epithelial matrix elements.

HaCaT cells were grown for 24 hours on glass coverslips for immunofluorescence microscopy either in normal medium, medium conditioned for 48 hours with 804G cells, or in co-culture (1:1) with 804G cells. The cells were fixed for 5 minutes in $-20°$ C. methanol, washed in PBS and immunolabeled with the following antibodies:

(1) AA3; a mouse monoclonal antibody to the human integrin subunit (Tamura, et al., *J. Cell Biol.* 1990; 111:1593-1604). This antibody specifically binds to human integrin molecules.

(2) GOH3; a rat monoclonal antibody to the $\alpha_6$ integrin subunit (AMAC, Westbrook, Me.). This antibody reacts with human and mouse, but not rat integrin molecules.

(3) 6844; a rabbit polyclonal antiserum to the cytoplasmic terminal 15 amino acids of the $\alpha_6$ integrin subunit.

(4) J18; a rabbit antiserum to the solubilized matrix of 04G cells (Langhofer, et al., (1993) *J. Cell Sci.,* 105:753-764.

(5) 5C5; a mouse monoclonal antibody the solubilized matrix of 804G cells.

(6) J17; a rabbit antiserum against the 180 kD hemidesmosomal protein (Riddelle et al., (1992) *J. Cell Sci.,* 103:475-490).

(7) P1E1; a mouse monoclonal antibody to epiligrin (from Dr. William G. Carter, Fred Hutchinson Cancer Research Center, Seattle, Wash., Carter, et al. 1991).

(8) BM165; a mouse monoclonal antibody to kalinin (from Dr. Robert E. Burgeson, Oregon Health Sciences University, Portland, Oreg., Rousselle, et al., 1991, Marinkovich, et al. 1992).

(9) GB3; a mouse monoclonal antibody to human basement membranes (from Accurate Chemical and Scientific Corporation, Westbury, N.Y., Verrando et al., (1987) *Exp. Cell Res.,* 170:16-128; Verrando et al., (1988) *Biochim. Biophys. Acta.,* 942:45-56.

Fluorescein isothiocyanate (FITC) or tetramethylrhodamine isothiocyanate (TRITC) conjugated antimouse and anti-rabbit antibodies were purchased from Jackson Immunoresearch Laboratories Inc. (West Grove, Pa.). FITC or TRITC conjugated anti-rat antibodies were from Sigma Chemical Corporation (St. Louis, Mo.).

After single or double immunolabeling the cells were studied under a Zeiss Axlophot microscope equipped with epifluorescence and phase contrast optics. Photographs were taken with a Leitz Orthomat E automatic camera system and Kodak TMY 400 film at EI 800.

The visualization and photography of living cells was performed with a Zeiss Axiovert microscope equipped with phase contrast optics and the same camera system as above.

In cells grown in normal medium, the $\alpha_6$ and $\beta_4$ integrin subunits had a patchy, finely granular distribution most clearly visualized at the edges of cell islands. In cells grown in the 804G supernatant, the $\alpha_6$ and $\beta_4$ subunits were reorganized into coarsely granular or "Swiss-cheese" type patterns. The same patterns were reflected in immunolabeling with any of the antibodies against epithelial matrix elements (P1E1, GB3, BM165) and with the antibody against the 180 kD hemidesmosomal protein (J17).

EXAMPLE 3

Electrophoretic Analysis of the Culture Medium

Polypeptide samples from the culture medium and solubilized matrix from 804G and HaCaT cells were analyzed by SDS-polyacrylamide gel electrophoresis on a 6% resolving gel (Laemmli 1974) with the NOVEX (Encinitas, Calif.) electrophoresis system. The separated polypeptides of culture medium, or purified rat laminin and fibronectin (as controls, Telios Pharmaceuticals/GIBCO, Grand Island, N.Y.) were electrophoretically transferred to Immobilon-P membranes (Millipore Corporation, Bedford, Mass.) and processed for immunoblotting with J18 and 5C5 antibodies. As controls, the polypeptides were immunoblotted with rabbit antiserum against rat laminin or rat fibronectin (Telios Pharmaceuticals). The Vectastain ABC immunoperoxidase or alkaline phosphatase were used to detect binding. (Vector Laboratories, Burlingame, Calif.).

The polyclonal antibody, J18 reacted with these polypeptides in immunoblotting experiments. Immunoblotting revealed further that the antibody did not cross-react with laminin or fibronectin, two common extracellular matrix molecules. However, the 804G cell matrix and medium do contain fibronectin, but only trace amounts of laminin-related material.

The monoclonal antibody 5C5 also reacts with the major polypeptides in 804G matrix. Immunoblotting of the HaCaT matrix reveals the same three 160–138 kD polypeptides as in the 804G matrix with an additional polypeptide having a molecular weight of approximately 130 kD. The 5C5 antibody is specific to rat proteins and therefore does not react with the HaCaT cell matrix grown in normal conditions.

In the culture medium of 804G cells the Mr 160–138 polypeptides are not clearly discernible by protein staining but can, instead, be identified by fluorography of metabolically S-labeled proteins.

EXAMPLE 4

Metabolic Labeling of 804G Cells

Metabolic labeling with $^{35}$S-methionine was performed by first incubating the cells for 30 minutes in starving medium (MEM-medium without methionine, supplemented with 1% dialyzed FCS, L-glutamine and antibiotics, GIBCO, Grand Island, N.Y.), and then replacing the medium with 3 ml of fresh MEM without methionine, supplemented with 1% dialyzed FCS and 250 μCi S-methionine (Tran S-Label ICN Biomedicals Inc., Costa Mesa, Calif.) for 10 hours.

Gels with radioactively labeled polypeptides were processed for fluorography according to Bonner and Laskey (1974) and exposed to Hyperfilm (Amersham Corporation, Arlington Heights, Ill.).

The incorporation of $^{35}$S-methionine indicated that the polypeptides were synthesized by the cells and not simply deposited into the matrix from the culture medium. Moreover, the polypeptides can be visualized by immunoblotting with J18 and 5C5 antibodies. When HaCaT cells are grown in 804G Cell supernatant, and their matrix is processed for immunoblotting with 5C5, two reactive polypeptides can be identified indicating that the soluble immunoreactive material from 804G supernatant is able to bind to the matrix of HaCaT cells.

The effect of the soluble 804G cell components on HaCaT cells was also evident at the ultrastructural level. When HaCaT cells are grown on cell culture plastic in normal culture medium, they attach to their growth substratum by means of extracellular matrix contacts that resemble rudimentary hemidesmosomes. Alternatively, when the cells were grown in 804G cell supernatant, they formed adhesion complexes that are by morphological criteria mature hemidesmosomes.

EXAMPLE 5

Immunodepletion of 804G Supernatant with J18 Antibodies

When the cells were grown in 804G supernatant immunodepleted with J18 antibody, only occasional hemidesmosomes can be identified at the ventral plasma membrane. Immunodepletion of 804G supernatant was carried out by treating 1 ml of supernatant three consecutive times with the J18 antibody coupled to 50 μl protein A SEPHAROSE ® beads (2 μg antiserum/10 μl packed beads, Sigma Chemical Corporation). As a control, 804G supernatant was also depleted with normal rabbit serum coupled to protein A coupled to cross-linked dextran (SEPHAROSE ®). The cells were fixed in modified Karnowsky fixative (1% paraformaldehyde, 0.1M Na-cacodylate, 1.75% glutaraldehyde, 2.5 mM CaCl) and processed for electron microscopy by routine methods. Thin sections were cut perpendicular to the cell layer and studied at 75 kV in a Hitachi Hu-12A microscope. The specificity of this effect is verified by the fact that immunodepletion with normal rabbit serum does not affect the hemidesmosome inducing potential of 804G supernatant.

To facilitate purification of secreted proteins, the 804G cell line was adapted to grow under low serum conditions as described in the following example.

EXAMPLE 6

Growth of 804G cells under low serum conditions 804G cells were gradually adapted to grow in 1:1 DMEM:OPTI-MEM (GIBCO, Grand Island, N.Y.) supplemented with 1% FCS, 2 mM glutamine, 100 μg/ml penicillin and 50 μg/ml streptomycin. The resulting 804G cell subpopulation was named 804GMH. According to the manufacturer, OPTI-MEM contains low amounts of transferrin and insulin, molecular weights 80 and 6 kDa, respectively, but no other proteins.

The virtual absence of serum proteins in the culture medium simplifies the purification of hemidesmosome-inducing soluble factors as described below.

EXAMPLE 7

Purification of soluble factors from 804GMH culture medium

For the collection of serum-free culture supernatant, confluent 804GMH cells grown under low serum conditions were removed by trypsinization (0.02%), washed once with DMEM containing 10% FCS and cultured in DMEM:OPTI-MEM with no added FCS at a split ratio of 1:6. Culture supernatant was collected when 804GMH cells had been confluent for 24 hours. The supernatant was centrifuged at 5,000×g for 10 minutes and stored at −20° C. until use. Secreted proteins were purified by precipitation with ammonium sulfate at 40% saturation. Culture supernatant (1 liter) was cleared of particulate material by centrifugation at 10,000×g for 30 minutes and transferred to another container on ice. Ammonium sulfate was slowly added, with stirring, to 30% saturation. The supernatant was then left at 4° C. overnight to allow complete precipitation. The sample was centrifuged for 30 min at 10,000×g and ammonium sulfate added to a final concentration of 40% saturation. After precipitation and centrifugation, the supernatant was discarded and the pellet resuspended in 1 ml PBS. The protein was dialyzed against PBS, the protein concentration estimated by absorbance at 280 nm, and an aliquot analyzed by SDS-PAGE. Bands of 240, 150 and 140 kDa were observed.

Thus, we have demonstrated that soluble factors produced by 804G cells are able to induce attachment and hemidesmosome assembly in mammalian cells and that the purification of these proteins from the culture medium is greatly facilitated by growing the cells under low serum conditions.

It should be noted that the present invention is not limited to only those embodiments described in the Detailed Description. Any embodiment which retains the spirit of the present invention should be considered to be within its scope. However, the invention is only limited by the scope of the following claims.

We claim:

1. A method for culturing mammalian epithelial cells in vitro comprising:
    culturing 804G rat bladder carcinoma cells in media under conditions that promote the secretion of soluble factors, wherein said 804G cells secrete said factors;
    removing said media from said 804G cells; and
    culturing said media with said epithelial cells, under conditions effective for hemidesmosome formation in said epithelial cells.

2. The method of claim 1 wherein said mammalian cells are human.

3. The method of claim 1 wherein said epithelial cells are human skin cells.

* * * * *